United States Patent [19]

Mehra et al.

[11] Patent Number: 4,744,987

[45] Date of Patent: May 17, 1988

[54] COPROCESSED MICROCRYSTALLINE CELLULOSE AND CALCIUM CARBONATE COMPOSITION AND ITS PREPARATION

[75] Inventors: Dev K. Mehra, Furlong; Kenneth P. West, Devon, both of Pa.; J. Donald Wiggins, Princeton Junction, N.J.

[73] Assignee: FMC Corporation, Philadelphia, Pa.

[21] Appl. No.: 81,584

[22] Filed: Aug. 3, 1987

Related U.S. Application Data

[63] Continuation of Ser. No. 709,748, Mar. 8, 1985, abandoned.

[51] Int. Cl.$^4$ ............ A61K 9/14; A61K 33/10; C08L 1/00; C09J 3/04
[52] U.S. Cl. ............ 424/156; 424/500; 514/781; 106/203; 106/204; 106/163.1
[58] Field of Search ............ 106/203, 204, 163.1; 424/500, 156; 514/781

[56] References Cited

U.S. PATENT DOCUMENTS

| | | | |
|---|---|---|---|
| 2,574,210 | 11/1951 | Guardiola-Aragonès | 106/203 |
| 2,599,091 | 6/1952 | Craig | 106/204 |
| 2,978,446 | 4/1961 | Battista et al. | 536/56 |
| 3,146,168 | 8/1964 | Battista | 424/107 |
| 3,539,365 | 11/1970 | Durand et al. | 106/197.2 |
| 3,827,899 | 8/1974 | Zirlin | 106/204 |
| 4,159,345 | 6/1979 | Takeo et al. | 514/781 |
| 4,310,520 | 1/1982 | Narazaki | 514/781 |
| 4,323,400 | 4/1982 | Henning | 106/163.1 |
| 4,391,973 | 7/1983 | Cruz | 106/203 |
| 4,446,135 | 5/1984 | Fountaine | 424/156 |
| 4,452,722 | 6/1984 | Turbak et al. | 106/203 |
| 4,489,026 | 12/1984 | Yalkowsky | 424/465 |
| 4,517,179 | 5/1985 | Raghunathan | . |
| 4,588,589 | 5/1986 | Sheth et al. | 514/57 |
| 4,605,551 | 8/1986 | Buehler et al. | 424/154 |
| 4,666,716 | 5/1987 | Sheth et al. | 424/195.1 |
| 4,666,919 | 5/1987 | Ueno et al. | 514/970 |

FOREIGN PATENT DOCUMENTS

WO81/2521 9/1981 PCT Int'l Appl. .

OTHER PUBLICATIONS

Chemical Abstracts: vol. 81, No. 16 (Oct. 21, 1974) p. 324, Abstract No. 96411f.

J. F. Bavitz & J. B. Schwartz "Direct Compression Vehicles" Drug & Cosmetic Industry 114, 44 (Apr. 1974).

J. B. Schwartz & J. F. Bavitz "Direct Compression Vehicles" Drug & Cosmetic Industry 118, 60 (Apr. 1976).

*Primary Examiner*—Ronald W. Griffin
*Attorney, Agent, or Firm*—Christopher Egolf

[57] ABSTRACT

A particulate coprocessed microcrystalline cellulose and calcium carbonate composition having the respective components present in a weight ratio of from about 75:25 to 35:65. The composition is useful as a pharmaceutical excipient.

The coprocessed composition is prepared by forming a well-dispersed aqueous slurry of microcrystalline cellulose and calcium carbonate and then drying the slurry, preferably by spray drying, to yield a particulate product.

24 Claims, No Drawings

COPROCESSED MICROCRYSTALLINE CELLULOSE AND CALCIUM CARBONATE COMPOSITION AND ITS PREPARATION

This application is a continuation of application Ser. No. 709,748 filed 3/8/85, now abandoned.

BACKGROUND OF THE INVENTION

1. Field of the Invention

This invention relates to a particulate composition that contains microcrystalline cellulose and calcium carbonate and which is useful as an excipient in pharmaceutical formulations.

More particularly, microcrystalline cellulose and calcium carbonate are processed together in an aqueous medium and dried to yield a particulate excipient product.

2. Description of the Prior Art

Microcrystalline cellulose is a purified, partially depolymerized cellulose that is prepared by treating alpha cellulose, in the form of a pulp manufactured from fibrous plant material, with mineral acids. It is a white, odorless, tasteless, relatively free flowing powder that is insoluble in water, organic solvents, dilute alkalis and dilute acids. U.S. Pat. Nos. 2,978,446 issued to Battista et al. and 3,146,168 issued to Battista are basic patents describing microcrystalline cellulose and its manufacature; the latter patent concerns microcrystalline cellulose for pharmaceutical applications.

Microcrystalline cellulose finds widespread use as a pharmaceutical excipient, an inactive (non-drug) ingredient in pharmaceutical formulations. Its inherent compressibility characteristics account for its popularity as a pharmaceutical excipient, since good binding and disintegration properties are obtained with microcrystalline cellulose when used in direct compression tablet formulations.

Compared to other tablet additives like partially pregelatinized cornstarch, lactose, and dicalcium phosphate, microcrystalline cellulose exhibits superior compressibility and disintegration properties. Unlike these additives, microcrystalline cellulose is relatively costly to manufacture; this limits its use in price-sensitive formulations like vitamins.

A lower cost excipient which has tabletting characteristics similar to those of microcrystalline cellulose would satisfy a need for an economical excipient with good performance that is desired by the vitamin market.

Physical blends of microcrystalline cellulose with starch, lactose of dicalcium phosphate, do not provide the desired performance characteristics. Microcrystalline cellulose coprocessed with either starch or calcium sulfate, as described by Schwartz et al. in Drug & Cosmetic Industry 118, 60 (April 1976) and 114, 44 (April 1974), offers direct compression tabletting performance that falls short of that for microcrystalline cellulose alone.

The present invention accomplishes this objective with microcrystalline cellulose that is coprocessed with a second, inexpensive component in a manner that yields a particulate product with unexpectedly good excipient performance characteristics.

SUMMARY OF THE INVENTION

In accordance with the present invention, a composition of matter useful as a pharmaceutical excipient is provided by particulate coprocessed microcrystalline cellulose and calcium carbonate, the two components being present in a weight ratio of from about 75:25 to 35:65 microcrystalline cellulose:calcium carbonate. The microcrystalline cellulose and calcium carbonate are intimately associated in the coprocessed particulate product and may be present as agglomerates of the two components.

The particulate coprocessed composition is preferably a spray dried material. Particle size of the coprocessed product should be substantially all less than No. 60 sieve (250 μm) and preferably has an average particle size in the range of from 20 μm to 150 μm.

The particulate coprocessed composition is prepared by forming a well-dispersed aqueous slurry of microcrystalline cellulose and calcium carbonate, both being present in particulate form and in amounts which provide a component ratio in the range of from 75:25 to 35:65 microcrystalline cellulose:calcium carbonate for the coprocessed product; and drying the aqueous slurry by removing water therefrom, to yield a particulate coprocessed product.

The aqueous well-dispersed slurry of the two components is preferably formed by introducing microcrystalline cellulose and calcium carbonate into an aqueous medium, with their addition being in the order mentioned, in amounts that yield a relatively concentrated slurry of at least 10 wt % solids. The aqueous slurry is preferably dried by spray drying to yield the particulate coprocessed product.

DETAILED DESCRIPTION

The particulate coprocessed product of this invention contains two essential components, microcrystalline cellulose and calcium carbonate. The two components are present in the product in a weight ratio in the range of about 75:25 to 35:65 microcrystalline cellulose:calcium carbonate. The ratio of the two components is preferably in the range of about 70:30 to 40:60 microcrystalline cellulose:calcium carbonate, and most preferably, in the range of about 65:35 to 50:50 microcrystalline cellulose:calcium carbonate.

Other ingredients may also be incorporated into the particulate product during its preparation. These are ordinarily present in relatively small amounts, representing less than 20%, and preferably less than 10%, of the total particulate product weight. Such additives may be incorporated to facilitate the coprocessing procedure, particularly during the drying step, or to provide enhanced properties for the particulate product in its use as a pharmaceutical excipient. Examples of additives in these categories are binders, e.g., water-soluble gums like hydroxypropylmethylcellulose, methylcellulose, polyvinylpyrrolidone, etc.; lubricants, e.g., long chain fatty acid esters or salts thereof like palmitic and stearic acids; and disintegrants like cross-linked carboxymethylcellulose, starch, etc.

The particulate coprocessed product of this invention possesses desirable performance attributes that are not shown with the corresponding dry-blend of microcrystalline cellulose and calcium carbonate. The mechanism that occurs during the coprocessing procedure required in this invention is not fully understood but appears to yield a particulate product in which the two essential components are in intimate association with each other. This intimate association or admixture of microcrystalline cellulose and calcium carbonate cannot be achieved through simple dry blending of these materials, but rather requires that they be coprocessed as an aqueous slurry or mixture.

This intimate association of the two components manifests itself in the appearance of agglomerated particles, containing both microcrystalline cellulose and calcium carbonate, that result after drying of the slurry.

Various characteristics of the particulate coprocessed product, e.g. its particle size, moisture content, bulk density, will be described in detail below, in the context of the process by which this particulate product may be prepared. These physical characteristics are in large measure dependent on the manner in which the microcrystalline cellulose and calcium carbonate are coprocessed. It is for this reason that the drying step in the coprocessing procedure is especially critical, and it is the reason that spray-drying is the preferred method for accomplishing the drying step.

In simple terms, the process for preparing the particulate product of this invention involves forming a well-dispersed aqueous slurry of microcrystalline cellulose and calcium carbonate, in which both materials are present as particulate solids. The relative amounts of the two components are adjusted in the slurry to yield the specific weight ratio desired in the recovered coprocessed product. Since the weight ratio of the two components in the particulate coprocessed product corresponds closely to that in the precursor well-dispersed slurry, this ratio adjustment is relatively straightforward.

The process of this invention next involves drying the aqueous slurry by removing water from it to yield the particulate coprocessed product. As mentioned earlier, spray drying is the preferred drying means but other drying methods, e.g. flash drying or fluidized bed drying, may also be adapted for use in this coprocessing step.

The two components employed in forming the well-dispersed aqueous slurry are microcrystalline cellulose and calcium carbonate. The source and nature of these components are not critical. The microcrystalline cellulose is preferably wet cake from a conventional microcrystalline cellulose manufacturing process. The wet cake is material which has not yet been dried, sometimes termed "never dried" or hydrocellulose, to yield a conventional microcrystalline cellulose free-flowing powder product. The microcrystalline cellulose source may also be conventional product, which has already been dried.

Particle size of the microcrystalline cellulose used in the aqueous slurry is ordinarily that which is encountered in conventional microcrystalline cellulose product, or in its precursor wet cake, i.e., never dried product. The particle size is desirably such that substantially all particles are less than No. 60 sieve (250 $\mu$m) in size.

Specific size requirements for fine particle sizes, if desired, can be met through screening off unwanted coarse material or through conventional wet or dry attrition procedures. Such attrition may also be accomplished with the microcrystalline cellulose in the aqueous slurry. These size reduction procedures are ordinarily not required with microcrystalline cellulose as is now commercially produced.

The calcium carbonate ($CaCO_3$) employed in this invention is preferably a precipitated material. Precipitated calcium carbonate is ordinarily more pure than ground calcium carbonate and typically has a finer particle size. Ground calcium carbonate may nevertheless be used as a source with satisfactory results.

The particulate calcium carbonate is preferably finer in particle size than the particulate microcrystalline cellulose with which it is coprocessed. Extremely fine particle size calcium carbonate is more readily combined in intimate association with the microcrystalline cellulose during coprocessing of the two components.

Calcium carbonate sizing is preferably such that substantially all particles are less than 30 $\mu$m in size and, more preferably, less than 10 $\mu$m. Average particle size of the calcium carbonate is desirably less than 5 $\mu$m and, more preferably, is less than 2 $\mu$m.

Both microcrystalline cellulose and calcium carbonate, it should be recognized, are substantially insoluble in water. Consequently, the particle size of the material present in the well-dispersed aqueous slurry is directly related to the sizing of the two components introduced to the slurry; i.e., there is no appreciable dissolution of either of the two components in the aqueous slurry.

The aqueous slurry of these two components may be prepared in any of several ways. The two solid components may both be introduced into a single aqueous medium, or each may be introduced separately into separate aqueous media which are then combined, or other analogous procedures may be devised.

A preferred procedure involves dispersing the microcrystalline cellulose alone into an aqueous solution, preferably water. Typical solids concentrations for this aqueous mixture are from 5-25 wt % microcrystalline cellulose but 10-20 wt % microcrystalline cellulose is preferred.

Once the microcrystalline cellulose is well-dispersed in the aqueous slurry, the appropriate amount of calcium carbonate is then added, in dry form, with mixing being continued during its addition. The exact amount of calcium carbonate to be added depends on the microcrystalline cellulose content of the slurry and the ratio of the two components desired in the coprocessed product. Water may also be added if a more dilute slurry is desired, but this is usually not required.

The aqueous slurry containing the two components should be well mixed to assure uniform dispersion of the components throughout the aqueous medium. This is necessary to provide for a uniform, consistent component ratio in the particulate product, prepared via drying the aqueous slurry.

The total solids content of the aqueous slurry is preferably at least 10 wt %, based on the total slurry weight, and is more preferably at least 20 wt % solids. The higher solids content levels are desirable since the amount of water that must be removed during the drying step is accordingly reduced.

The upper limit on solids content in the aqueous slurry is typically determined by the operating constraints of the drying apparatus used. With the preferred spray drying procedure, solids contents of 20-30 wt % are representative for aqueous slurries that can be readily processed.

Temperature of the aqueous slurry is not critical. Ambient temperatures, of from about 10°-25° C., are preferred. Higher slurry temperatures may be employed, and these may be desirable with certain types of drying equipment.

The drying of the well-dispersed aqueous slurry is preferably accomplished by spray drying of the slurry. Conventional spray drying equipment may be employed, and operating procedures that are familiar to those experienced in the spray drying art are applicable to the spray drying step of this process. Drier (drier gas)

outlet temperature is ordinarily used to control the residual moisture level obtained in the coprocessed particulate product.

Moisture levels of about 1–8 wt % $H_2O$ are desired in the particulate, dried product and moisture levels of about 3–7 wt % are most preferred. These levels are based on the finding that the coprocessed product, if completely dried (no residual moisture), will usually absorb moisture from the atmosphere, in amounts within these specified ranges.

In a spray drying procedure, drier outlet temperatures are ordinarily in the range of about 40°–100° C. Corresponding drier inlet temperatures are higher, ordinarily in the range of about 90°–300° C.

The coprocessed product recovered from the drying operation is a free-flowing particulate solid, that is typically a granular white powder in appearance. Particle size of the product is a function of the particle sizing of the microcrystalline cellulose and calcium carbonate in the aqueous slurry and, more importantly, of the drying conditions employed for removing water from the slurry.

The particulate coprocessed product should have a particle size that is substantially all less than No. 60 sieve (250 μm). Average particle size of the particulate material is preferably in the range of from about 20 μm to 150 μm, and more preferably is in the range of from about 30 μm to 100 μm.

Bulk density (loose) of the coprocessed product, with a preferred component ratio of 60:40 microcrystalline cellulose:calcium carbonate, typically is in the range of about 0.35–0.45 g/cm³; microcrystalline cellulose ordinarily exhibits a loose bulk density of around 0.28–0.30 g/cm³.

An aqueous slurry of the coprocessed product with the preferred component ratio of 60:40 exhibits a moderately alkaline pH around 9.5–10, whereas microcrystalline cellulose in an aqueous slurry has a pH of around 6.5–7.

The particulate coprocessed product of this invention, besides being economical, has several desirable properties that make it particularly well-suited for use as an excipient for vitamins, in direct compression tabletting applications.

The coprocessed microcrystalline cellulose/calcium carbonate product exhibits low lubricant sensitivity; its compression profile (tablet hardness vs. tablet compression force) remains relatively unchanged when various lubricants are employed with the excipient. This lubricant insensitivity extends both to lubricant level (amount) and lubricant type (magnesium stearate, stearic acid, etc.). The compression force required to produce a specific tablet hardness does not change when lubricants are employed with the coprocessed excipient of this invention.

By contrast, the compression profile for pure microcrystalline cellulose is adversely affected by the introduction of lubricants, with higher compression forces being required to produce the same tablet hardness as for the equivalent lubricant-free tablets.

Flow characteristics of the particulate coprocessed material are good, and its use in conventional direct compression tabletting equipment does not present operating difficulties due to the material's particle flow behavior.

The compressibility of this coprocessed product compares favorably with that of commercially available microcrystalline celluloses. Compressibility is typically measured as the profile, or shape, of the plot of tablet hardness vs. tablet compression force. Compressibility of a excipient is desirably high, since low levels of excipient may then be used in tabletting an active ingredient (with concurrent larger amounts of active ingredient being present) without compromising tablet performance characteristics.

The compressibility profile of a 60:40 microcrystalline cellulose:calcium carbonate coprocessed product is very similar to that of microcrystalline cellulose available from Ming Tai and designated 101 grade. Both of these are less compressible than Avicel®PH-101 microcrystalline cellulose, a commercial product manufactured by FMC Corporation.

EXAMPLE

The Example describes the preparation of a particulate coprocessed microcrystalline cellulose and calcium carbonate product having the two components present in a weight ratio of about 60:40. The particulate coprocessed composition is prepared by spray drying, a preferred drying procedure.

In the preparation of this product, a well-dispersed aqueous slurry of microcrystalline cellulose and calcium carbonate is first formed. Microcrystalline cellulose, material obtained from a conventional microcrystalline cellulose manufacturing process as moist product filter cake that has not been dried, is introduced into water at about 20° C. in a sufficient amount to yield an aqueous slurry containing about 17–18 wt % solids.

The microcrystalline cellulose that is employed to make the slurry is particulate in form, but exact sizing is difficult to measure due to its being a moist filter cake.

Calcium carbonate, a precipitated fine powder having an average particle size of about 1 μm (USP Albaglos precipitated calcium carbonate from Pfizer, Inc.), is introduced into the microcrystalline cellulose slurry in an amount corresponding to two-thirds of the amount (weight) of the microcrystalline cellulose.

The aqueous slurry, containing about 25 wt % solids, is thoroughly mixed so as to assure homogeneous dispersion of the two solid components throughout the slurry.

The well-dispersed slurry is then fed continuously to a Koch 40 ft. diameter spray drier, in which the drier inlet and outlet temperatures are maintained at about 180° C. and 70° C., respectively.

The particulate spray-dried coprocessed material recovered from spray drying contains a 59–41 weight ratio of microcrystalline cellulose:calcium carbonate. The free-flowing white powder has a loose bulk density of about 0.39–0.40 g/cm³, is substantially all smaller than No. 60 sieve (250 μm), and has an average particle size of about 61 μm. The spray drying temperature conditions and slurry feed rate yield a particulate product that contains about 3 wt % $H_2O$.

Particulate spray-dried coprocessed product prepared in the manner just described may be employed as an excipient in vitamin or other pharmaceutical formulations intended for direct compression tabletting. The procedure for such use in direct compression tabletting is conventional: blend the excipient in the desired amount with the other dry ingredients to be tabletted; add lubricants, if desired, and continue blending a short period longer, e.g., five minutes; and compress the dry blend at the desired hardness setting in a tabletting machine.

We claim:

1. A composition of matter useful as a pharmaceutical excipient comprising dried particulate agglomerates of coprocessed microcrystalline cellulose and calcium carbonate, the two components being present in a weight ratio of from about 75:25 to 35:65 microcrystalline cellulose:calcium carbonate and intimately associated with each other.

2. The composition of claim 1, wherein the particulate material is spray-dried coprocessed microcrystalline cellulose and calcium carbonate.

3. The composition of claim 1 wherein the weight ratio of the two components is in the range of from about 70:30 to 40:60 microcrystalline cellulose:calcium carbonate.

4. The composition of claim 1 wherein the weight ratio of the two components is in the range of from about 65:35 to 50:50 microcrystalline cellulose:calcium carbonate.

5. The composition of claim 1 wherein the particle size of the coprocessed microcrystalline cellulose and calcium carbonate is substantially all less than No. 60 sieve (250 $\mu$m).

6. The composition of claim 1 wherein the particulate coprocessed microcrystalline cellulose and calcium carbonate has an average particle size in the range of from 20 $\mu$m to 150 $\mu$m.

7. The composition of claim 1 wherein the particulate, coprocessed microcrystalline cellulose and calcium carbonate has a moisture content of from 1–8 wt % $H_2O$.

8. A process for preparing a particulate material useful as a pharmaceutical excipient, which comprises
forming a well-dispersed aqueous slurry of microcrystalline cellulose and calcium carbonate, both being present in particulate form and in amounts which produce a component ratio within the range specified below for the particulate coprocessed product, and
drying the aqueous slurry by removing water therefrom to yield a particulate coprocessed product, in which the weight ratio of microcrystalline cellulose to calcium carbonate is in the range of from about 75:25 to 35:65.

9. A process for preparing a particulate material useful as a pharmaceutical excipient, which comprises
dispersing microcrystalline cellulose and calcium carbonate, both in particulate form, into an aqueous medium to form a well-dispersed aqueous slurry containing relative amounts of microcrystalline cellulose and calcium carbonate that provide a component ratio within the range specified below for the particulate coprocessed product, and
drying the aqueous slurry by removing water therefrom to yield a particulate coprocessed product, in which the weight ratio of microcrystalline cellulose to calcium carbonate is in the range of from about 75:25 to 35:65.

10. The process of claims 8 or 9 wherein the aqueous slurry is dried by spray drying.

11. A process for preparing a particulate material useful as a pharmaceutical excipient, which comprises the steps of
dispersing particulate microcrystalline cellulose into an aqueous medium in an amount of from about 5 to 25 wt % based on the slurry weight;
introducing particulate calcium carbonate into the aqueous microcrystalline cellulose slurry in an amount which provides a component ratio within the range specified below for the particulate coprocessed product;
dispersing the slurry solid components uniformly throughout the aqueous slurry, the amounts of solids previously introduced into the slurry being sufficient to provide a total solids content of at least 10 wt % based on total slurry weight; and
spray drying the well-dispersed slurry to yield a particulate coprocessed product, in which the weight ratio of microcrystalline cellulose to calcium carbonate is in the range of from about 75:25 to 35:65.

12. The process of claims 8, 9 or 11 wherein the weight ratio of microcrystalline cellulose to calcium carbonate is in the range of from about 65:35 to 50:50.

13. The process of claims 8, 9 or 11 wherein the drying conditions are adjusted to yield a dried particulate coprocessed product having a residual moisture content of from 1–8 wt % $H_2O$.

14. The process of claims 8, 9 or 11 wherein the drying conditions are adjusted to yield a dried particulate coprocessed product having particle size that is substantially all less than No. 60 Sieve (250 $\mu$m).

15. The process of claim 14 wherein the dried particulate coprocessed product has an average particle size in the range of from 20 $\mu$m to 150 $\mu$m.

16. The process of claims 8, 9 or 11 wherein the particulate microcrystalline cellulose is never-dried material from a microcrystalline cellulose manufacturing process.

17. The process of claims 8, 9 or 11 wherein the particulate calcium carbonate in the aqueous slurry is substantially finer than the particulate microcrystalline cellulose therein.

18. The process of claims 8, 9 or 11 wherein the particulate microcrystalline cellulose in the aqueous slurry has a particle size that is substantially all less than No. 20 Sieve (250 $\mu$m).

19. The process of claims 8, 9 or 11 wherein the particulate calcium carbonate is substantially all smaller than 30 $\mu$m.

20. The process of claims 8, 9 or 11 wherein the particulate calcium carbonate is substantially all smaller than 10 $\mu$m.

21. The process of claims 8, 9 or 11 wherein the average particle size of the particulate calcium carbonate is less than 5 $\mu$m.

22. The process of claims 8, 9 or 11 wherein the well-dispersed aqueous slurry to be dried has a solids content of at least 20 wt % solids, based on the total slurry weight.

23. The process of claim 11 wherein the spray drying operation is carried out with a drier outlet temperature in the range of from about 40°–100° C.

24. The process of claim 11 wherein the spray drying operation is carried out with a drier inlet temperature in the range of from about 90°–300° C.

* * * * *